United States Patent
Di Teodoro et al.

(10) Patent No.: US 6,596,907 B1
(45) Date of Patent: Jul. 22, 2003

(54) PROCESS FOR THE PREPARATION OF 4,4'-DIHALOGEN-O-HYDROXYDIPHENYL COMPOUNDS

(75) Inventors: Armando Di Teodoro, Rheinfelden (DE); Werner Hölzl, Eschentzwiller (FR); Dieter Reinehr, Kandern (DE); Rudolf Zink, Therwil (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/806,668

(22) PCT Filed: Sep. 27, 1999

(86) PCT No.: PCT/EP99/07157

§ 371 (c)(1),
(2), (4) Date: Apr. 3, 2001

(87) PCT Pub. No.: WO00/20365

PCT Pub. Date: Apr. 13, 2000

(30) Foreign Application Priority Data

Oct. 6, 1998 (EP) .............................. 98811003

(51) Int. Cl.$^7$ ...................... C07C 41/00; C07C 43/257
(52) U.S. Cl. ...................... 568/631; 568/635; 568/636; 568/637; 568/638
(58) Field of Search ................... 568/631, 635, 568/636, 637, 638

(56) References Cited

U.S. PATENT DOCUMENTS 2,777,002 A * 1/1957 Sullivan
3,904,696 A * 9/1975 Model et al.
6,215,029 B1 * 4/2001 Burckhardt et al.
6,239,317 B1 * 5/2001 Kulkarni et al.

FOREIGN PATENT DOCUMENTS

| CH | 428759 | 7/1967 |
| DE | 2242519 | 3/1974 |
| EP | 0857711 | 8/1998 |
| GB | 1415945 | 12/1975 |

OTHER PUBLICATIONS

C. A. Nilsson, Chemosphere, vol. 6, No. 5, (1977), pp. 249–262.
T. Humppi, Synthesis, (1985), pp. 919–924.

* cited by examiner

*Primary Examiner*—Samuel Barts
*Assistant Examiner*—Sikarl A. Witherspoon
(74) *Attorney, Agent, or Firm*—Kevin T. Mansfield

(57) ABSTRACT

A description is given of a three-step process for the preparation of 4,4'-dihalogen-o-hydroxydiphenyl compounds of formula (1) which comprises: a) hologenating an alkoxyphenol of formula (6) (=$a_1$), reacting the resulting halogenated phenol compound of formula (5) with p-dihalobenzene of formula (4a) in the presence of copper and/or copper salts to the diphenyl ether compound of formula (2) (=$a_2$) and subsequent ether fission to the diphenyl ether compound of formula (1) (=$a_3$); or b) reacting an alkoxyphenol of formula (6) with the halophenol of formula (4b) to the compound of formula (3) (=$b_1$), then halogenating this compound (=$b_2$) and subsequent ether fission of the resulting compound of formula (2) to the diphenyl ether compound of formula (1) (=$b_3$). The compounds of formula (1) are used for protecting organic materials and objects against microorganisms.

5 Claims, No Drawings

PROCESS FOR THE PREPARATION OF 4,4'-DIHALOGEN-O-HYDROXYDIPHENYL COMPOUNDS

This application is a 371 of PCT/EP99/07157 filed Sep. 27, 1999, published as WO 00/20365 on Apr. 13, 2000.

The present invention relates to the preparation of 4,4'-dihalogen-o-hydroxydiphenyl compounds of formula

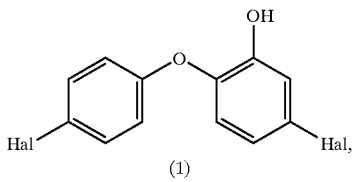

wherein

Hal is a halogen atom, and to the use of these compounds for protecting organic materials and objects against microorganisms.

The preparation of 4,4'-dihalogen-o-hydroxydiphenyl compounds is normally carried out by diazotisation and subsequent hydrolysis of 2-amino-4,4'-dichlorodiphenyl ether (compound of formula (1)).

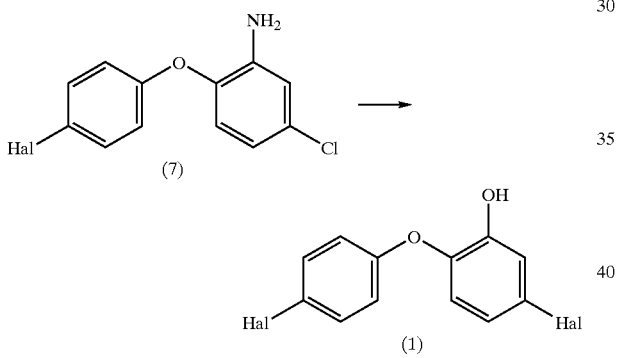

However, the yield obtained by this method of preparation is unsatisfactory as different chemical reactions may take place concurrently.

Accordingly, this invention has for its object to provide an economic process for the preparation of 4,4'-dihalogen-o-hydroxydiphenyl compounds in which undesirable concurrent reactions are suppressed.

This object is achieved in accordance with this invention by a three-step reaction, where in the first step either a) an alkoxyphenol of formula (6) is halogenated ($a_1$), the resulting halogenated phenol compound of formula (5) is reacted with a p-dihalobenzene of formula (4a) in the presence of copper and/or copper salts to the diphenyl ether compound of formula (2) ($a_2$) and the desired diphenyl ether compound of formula (1) is then obtained by ether fission ($a_3$), or b) an alkoxyphenol of formula (6) is reacted with the halobenzene of formula (4b) to the compound of formula (3) ($b_1$), which compound is then halogenated ($b_2$) and the resulting diphenyl ether compound of formula (2) is reacted by ether fission to the desired diphenyl ether compound of formula (1) ($b_3$), in correspondence with the following reaction scheme:

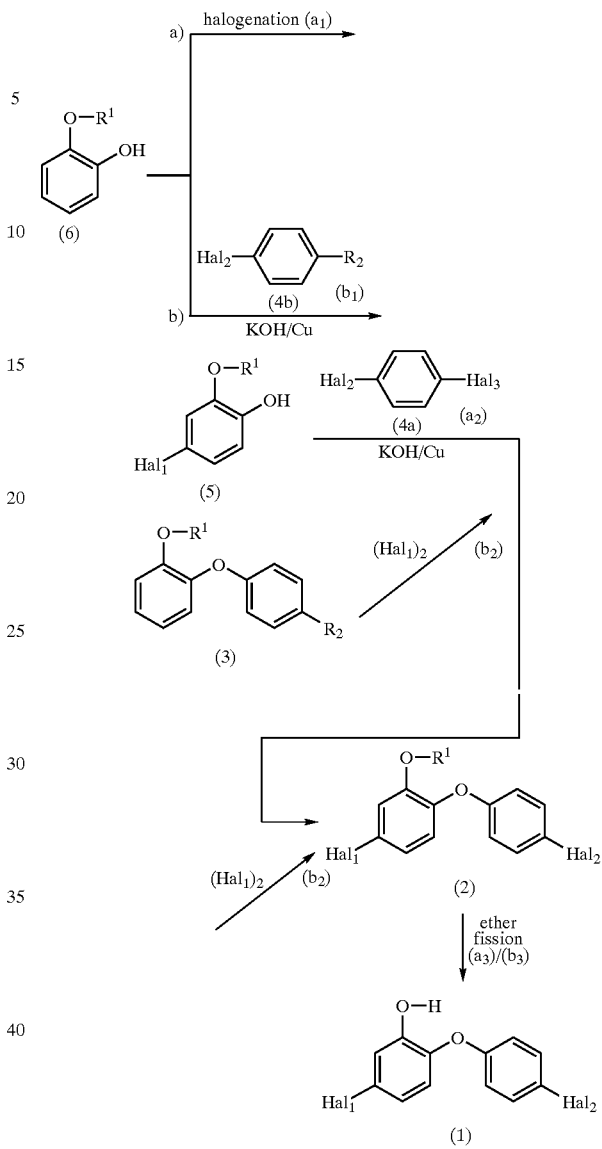

In the above scheme $R_1$ is $C_1$–$C_5$ alkyl;

$R_2$ is hydrogen; chloro or bromo; and $Hal_1$, $Hal_2$ and $Hal_3$ are each independently of one another a halogen atom.

$C_1$–$C_5$Alkyl is branched or unbranched alkyl, such as methyl, ethyl, propyl, isopropyl, n-butyl, sec-butyl, isobutyl, t-butyl, 2-ethylbutyl, or n-pentyl.

In the above reaction scheme, $R_1$ is preferably $C_1$–$C_4$alkyl, more preferably methyl.

$Hal_1$, $Hal_2$ are preferably bromo and very particularly preferably chloro.

$Hal_3$ is preferably chloro or bromo.

The halogenation of the alkoxyphenol of formula (6) to the phenol compound of formula (5) is preferably carried out using chlorine gas or sulfuryl chloride in the presence of an organic solvent, for example an aromatic, aliphatic or cycloaliphatic hydrocarbon, preferably with toluene or a xylene isomer mixture at a temperature in the range from −10 to 70° C., preferably from 20 to 35° C. The crude product of formula (5) so obtained is separated from the reaction mixture by neutralisation with sodium carbonate or potassium carbonate or by air being passed through the reaction mixture, the crude product of formula (5) then being collected by distillation under reduced pressure.

The reaction of the halogenated phenol compound of formula (5) with the dihalogen compound of formula (4a) (reaction ($a_2$)) and the reaction of the phenol compound of formula (6) with the dihalogen compound of formula (4b) (reaction ($b_1$)) is usually carried out at temperatures in the range from 120 to 200, preferably from 130 to 170° C., it being possible for the phenol compound of formula (5) and for the dihalogen compound of formula (4a) or (4b) to be present in stoichiometric ratio and for the alkali hydroxide to be present in less than equivalent amount (20 to 80% of theory).

The copper catalysts used are preferably the copper salts conventionally used for the Ullmann synthesis, for example copper(II) oxide, copper(I) oxide, copper carbonate, basic copper carbonate, copper(I) chloride, copper(II) chloride, copper(I) bromide, copper(II) bromide or copper sulfate.

Further details on this reaction step are to be found in DE-OS-2,242,519.

The ether fission (reaction ($a_3/b_3$)) is usually effected by treatment with $AlCl_3$ in an inert organic solvent, for example petroleum ether or benzene, or by heating with hydrobromic acid or mixtures of hydrobromic acid and acetic acid. The reaction time usually ranges from 0.5 to 10 hours and the temperature ranges from 40 to 110° C.

The inventive reaction route a) (=$a_1/a_2/a_3$) according to the following scheme is preferred:

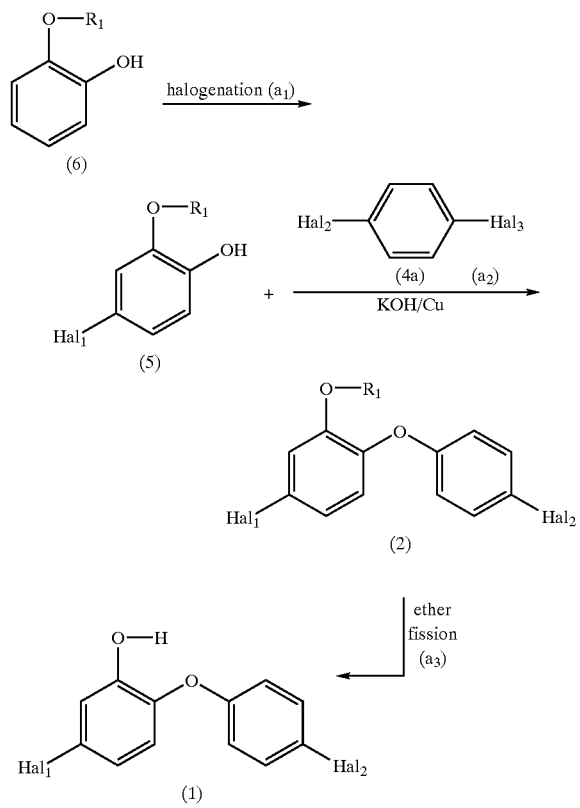

The 4,4'-dihalogen-o-hydroxydiphenyl compounds prepared according to this invention are insoluble in water, but are soluble in dilute sodium hydroxide and potassium hydroxide solution and in virtually all organic solvents.

Thanks to these solubility preconditions, they have very versatile applicability for fighting microorganisms, in particular bacteria, and for protecting organic materials and objects against microorganisms. These compounds can, for example, be applied to the human skin and hands and to hard objects in dilute or undiluted form together with e.g. wetting agents or dispersants, for example as soap or syndet solutions, for disinfection and cleansing.

The following non-limitative Examples illustrate the invention in more detail.

EXAMPLE 1

$1^{st}$ Reaction Step

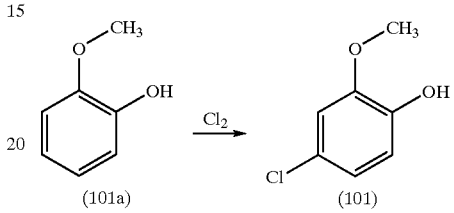

124 g of o-methoxyphenol and 200 ml of dry toluene are placed in a four-necked flask fitted with stirrer, condenser and dropping funnel.

148 g of sulfuryl chloride are added dropwise, with stirring, over about 1 hour, the temperature of the reaction mixture being kept at 20 to 25° C. After the addition is complete, stirring is continued at room temperature for 2 hours, after which time the reaction mixture is transferred to a separating funnel, shaken with 50 ml portions of 5% sodium carbonate solution, washed with 50 ml of water and dried over sodium sulfate. Subsequently, the sodium sulfate is removed by filtration and the chlorinated reaction product is subjected to distillation under reduced pressure.

This yields 144 g of 2-methoxy-4-chlorphenol having a melting point of 128 to 134° C. at 1999.8 Pa Hg.

Yield: 90.8% of theory.

EXAMPLE 2

$2^{nd}$ Reaction Step

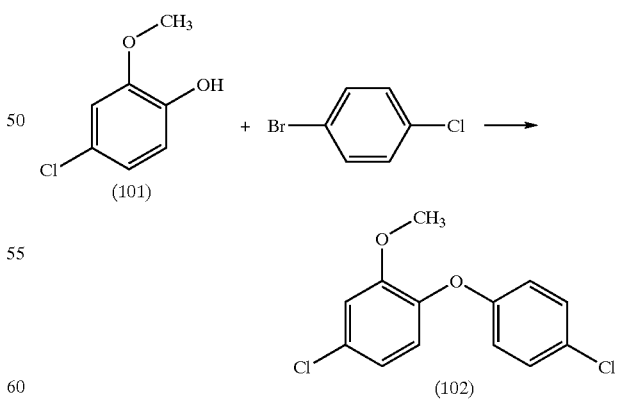

198.3 g of 4-chloro-2-methoxyphenol (compound of formula (101)) are placed in a vessel together with 209 g of a xylene isomer mixture and the resulting mixture is heated to 80° C. and charged with 27.5 g of (85%) KOH. This mixture is then heated to 145° C. and 9.5 ml of water are separated in a water separator over 2 hours. After cooling to 100° C., 1 g of basic copper carbonate and 239.4 g of 4-bromochlorobenzene are added successively. After stirring for 2.5 hours at 144–150° C., the mixture is cooled to room temperature and the potassium bromide formed is removed by filtration.

The solvent and the educts are then removed under vacuum. Distillation in an oil pump vacuum yields 67.6 g of a yellowish oil which quickly solidifies. Recrystallisation from petroleum ether yields a white, crystalline product of formula (102). m.p.=72–73° C.

EXAMPLE 3

Example 2 is repeated, but using 294 g of 1,4-dichlorobenzene instead of 239.4 g of 4-bromochlorobenzene. After a reaction time of 5 hours at 148° C. and after another 19 hours at 141° C. and working up, the compound of formula (102) is obtained in a yield of 44 g.

EXAMPLE 4

Ether Fission (3$^{rd}$ Reaction Step)
Reaction Scheme:

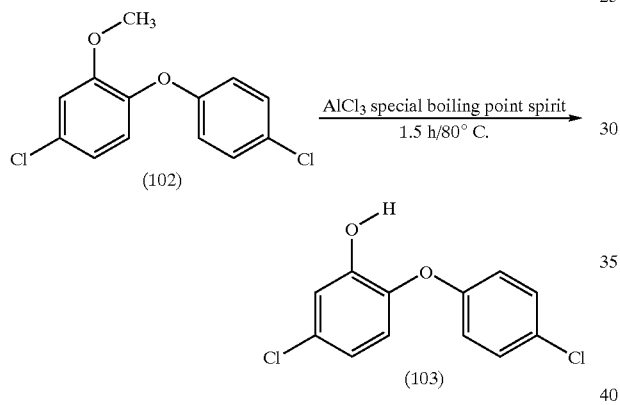

5.3 g of diphenyl ether of formula (102) are made into a slurry in 50 ml of petroleum ether at 80–110° C. and this slurry is then charged at room temperature with 6 g of anhydrous aluminium chloride and heated to 80° C. This temperature is maintained, with thorough stirring, for 1.5 hours until the ether fission is complete. The reaction mixture is added to 100 ml of hydrochloric acid 2N, stirred for 15 minutes at about 70° C. and subjected to phase separation. The solvent phase is clarified by warm filtration and the product is crystallised first at 25° C. and then for 1 hour at 5° C. and is then dried, yielding 2.3 g of a pure, white, crystalline product of formula (103) having a melting point of 73 to 74° C.

What is claimed is:

1. A process for the preparation of a 4,4'-dihalogen-o-hydroxydiphenyl compound of formula (1), which comprises
    a) halogenating an alkoxyphenol of formula (6) with a halogenating agent selected from the group consisting of elemental chlorine and sulfuryl chloride, in the presence of an aromatic, aliphatic or cycloaliphatic hydrocarbon in step ($a_1$), reacting the resulting halogenated phenol compound of formula (5) with a p-dihalobenzene of formula (4a) in the presence of copper and/or copper salts and alkali hydroxide to the diphenyl ether compound of formula (2) in step ($a_2$)

wherein the alkali hydroxide is used in less than an equivalent amount, with subsequent ether fission with $AlCl_3$ in an inert solvent to the diphenyl ether compound of formula (1) in step ($a_3$), or b) reacting an alkoxyphenol of formula (6) with the halobenzene of formula (4b) to the compound of formula (3) in step ($b_1$), halogenating this compound in step ($b_2$), with subsequent ether fission of the resulting compound of formula (2) with $AlCl_3$ in an inert solvent to the diphenyl ether compound of formula (1) in step ($b_3$), in correspondence with the following reaction scheme:

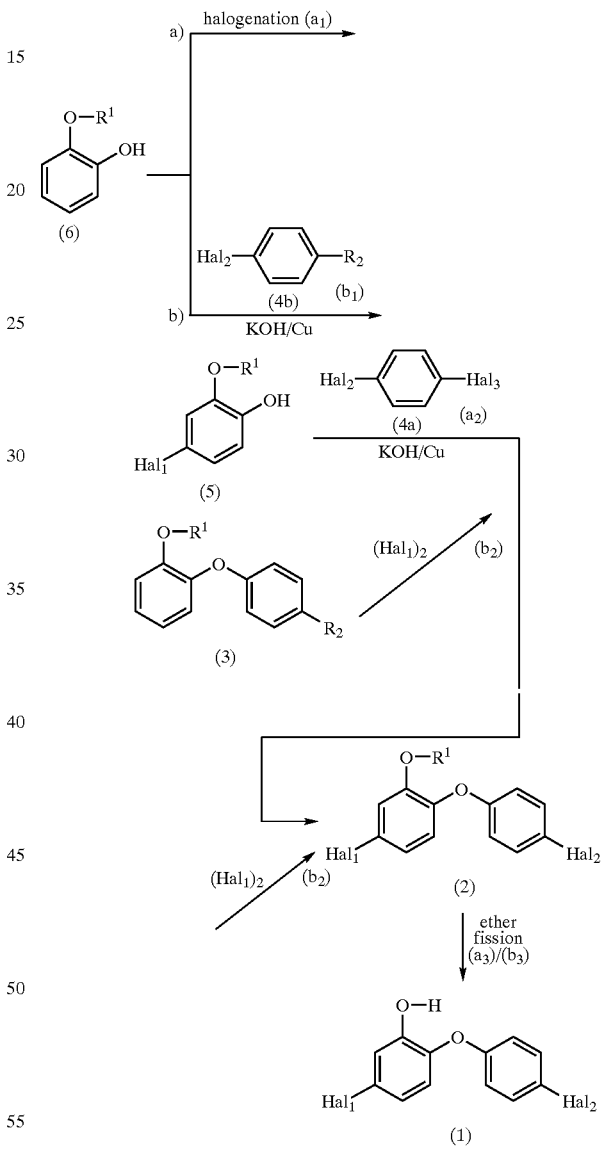

wherein
$R_1$ is $C_1$–$C_5$alkyl;
$R_2$ is hydrogen; chloro or bromo; and
$Hal_1$, $Hal_2$ and $Hal_3$ are each independently of one another a halogen atom.

2. A process according to claim 1, wherein $R_1$ is methyl.

3. A process according to claim 1, wherein $Hal_1$ and $Hal_2$ are chloro, and $Hal_3$ is bromo.

4. A process according to claim 1, wherein the copper catalysts used for the reaction step ($a_2$) or ($b_1$) are copper(II)

oxide, copper(I) oxide, copper carbonate, basic copper carbonate, copper(I) chloride, copper(II) chloride, copper(I) bromide, copper(II) bromide or copper sulfate.

5. A process according to claim 1, which comprises using reaction route a) comprising steps ($a_1$), ($a_2$) and ($a_3$) in accordance with the following scheme

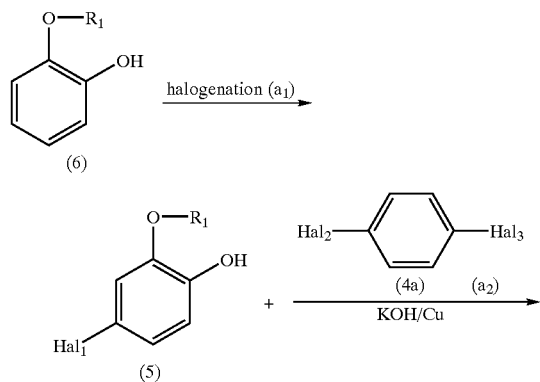

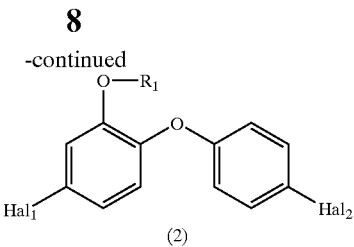

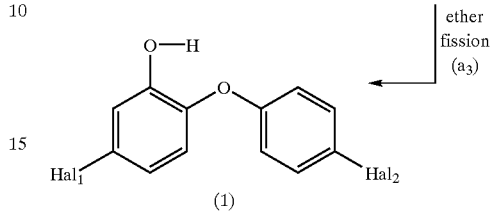

wherein
$R_1$ is $C_1$–$C_5$alkyl; and
$Hal_1$, $Hal_2$ and $Hal_3$ are each independently of one another a halogen atom.

* * * * *